United States Patent [19]

Kreis et al.

[11] 4,222,951
[45] Sep. 16, 1980

[54] ADDITION OF SI-BONDED HYDROGEN TO AN ALIPHATIC MULTIPLE BOND

[75] Inventors: Gerhard Kreis, Munich; Peter August, Seevetal, both of Fed. Rep. of Germany

[73] Assignee: Consortium für Elektrochemische Industrie GmbH, Munich, Fed. Rep. of Germany

[21] Appl. No.: 11,966

[22] Filed: Feb. 14, 1979

[30] Foreign Application Priority Data

Mar. 8, 1978 [DE] Fed. Rep. of Germany ....... 2809875

[51] Int. Cl.² ............................................. C07F 7/08
[52] U.S. Cl. ................................................... 556/478
[58] Field of Search ................................. 260/448.2 E

[56] References Cited

U.S. PATENT DOCUMENTS 3,631,086  12/1971  Seyfried et al. ............... 260/448.2 E Primary Examiner—Paul F. Shaver

[57] ABSTRACT

This invention relates to halogen platinum complexes of the formula $A_2PtX_2$ and/or $C_3H_6PtB_2X_2$ and a process for adding Si-bonded hydrogen to an aliphatic multiple bond in the presence of these halogen platinum complexes, in which A represents the same or different pyridine rings, which are substituted by one or two alkyl radicals having from 1 to 3 carbon atoms, B represents the same or different, 5- or 6-membered heterocyclics or linked 5- or 6-membered heterocyclics having 1 to 2 heteroatoms and X represents the same or different halogen atoms.

8 Claims, No Drawings

ADDITION OF SI-BONDED HYDROGEN TO AN ALIPHATIC MULTIPLE BOND

The present invention relates to hydrosilation catalysts and more particularly to a process for the addition of Si-bonded hydrogen to an aliphatic multiple bond using halogen platinum complexes as hydrosilation catalysts.

BACKGROUND OF INVENTION

Heretofore, it was generally known that "hydrosilation", i.e., the addition of Si-bonded hydrogen to an aliphatic multiple bond can be promoted with the aid of catalysts, such as platinum catalysts. Platinum catalysts, especially complexes of platinum have been described in U.S. Pat. No. 3,814,730 to Karstedt, for promoting the addition of an organosilicon material having a silicon bonded hydrogen atom to an aliphatically unsaturated material having either olefinic or acetylenic unsaturation to form an adduct having a new silicon-carbon linkage.

Compared to the catalysts known heretofore which promote the addition of Si-bonded hydrogen to an aliphatic multiple bond, the catalysts of this invention have the advantage that they are either reactive only at higher temperatures or that they are more effective than the catalysts known heretofore, but are promoting fewer side reactions at the same time.

Therefore it is an object of this invention to provide a catalyst which promotes the addition of Si-bonded hydrogen to an aliphatic multiple bond. Another object of this invention is to provide a catalyst which is reactive only at elevated temperatures. Still another object of this invention is to provide a catalyst which promotes the addition of Si-bonded hydrogen to an aliphatic multiple bond which is more efficient and more reactive than the catalysts of the prior art. A further object of this invention is to provide an effective catalyst for the addition of Si-bonded hydrogen to an aliphatic multiple bond but promotes fewer side reactions. A still further object of this invention is to provide a process for adding Si-bonded hydrogen to an aliphatic multiple bond in the presence of a halogen platinum complex catalyst.

SUMMARY OF INVENTION

The foregoing objects and others which will become apparent from the following description are accomplished in accordance with this invention generally speaking by providing a process for adding Si-bonded hydrogen to an aliphatic multiple bond in the presence of at least one halogen platinum catalyst selected from the group consisting of complexes of the formulas $$A_2PtX_2, C_3H_6PtB_2X_2$$

and mixtures thereof, in which A represents the same or different pyridine rings, which are substituted by 1 or 2 alkyl radicals which are the same or different and have from 1 to 3 carbon atoms, B represents the same or different, 5- or 6-membered heterocyclics or linked 5- or 6-membered heterocyclics having 1 or 2 heteroatoms and X represents the same or different halogen atoms.

DETAILED DESCRIPTION OF INVENTION

In the halogen platinum complexes represented by the above formulas, X may represent fluorine, chlorine, bromine or iodine. However, because of its availability, it is preferred that X be chlorine.

Examples of ligands represented by A are alpha-picoline, beta-picoline, gamma-picoline, 2-ethylpyridine, 3-ethylpyridine, 4-ethylpyridine, 2-methyl-4-ethylpyridine and 4-n-propylpyridine.

Suitable examples of halogen-platinum complexes having the general formula $$A_2PtX_2,$$

in which A and X are the same as above, are bis-(alpha-picoline)-platinum dichloride, bis-(beta-picoline)-platinum dichloride, bis-(gamma-picoline)-platinum dichloride, bis-(2-ethylpyridine)-platinum dichloride, bis-(3-ethylpyridine)-platinum dichloride, bis-(4-ethylpyridine)-platinum dichloride, bis-(2-methyl-4-ethylpyridine)-platinum dichloride and bis-(4-n-propylpyridine)platinum dichloride.

Halogen-platinum complexes having the formula $A_2PtX_2$ can be prepared for example, by reacting a $K_2PtX_4$ compound, where X is the same as above, with a pyridine which is substituted by 1 to 2 alkyl radicals which may be the same or different and have from 1 to 3 carbon atoms, in a mol ratio of 1:2 in an aqueous solution at temperatures of from 25° to 70° C. The resultant complexes are primarily present in the cis form. The heterocyclics represented by B are preferably those containing oxygen or nitrogen or those containing 2 nitrogen atoms or 1 nitrogen atom and 1 oxygen atom as the heteroatoms. The previously cited examples of ligands represented by A are also applicable to the ligands represented by B. Additional examples of ligands represented by B are pyridine, tetrahydrofurfurylamine, 2-methylpiperidine, 4-methylpiperidine, 2,2'-bipyridyl, 2,6-dimethylmorpholine and tetrahydrofuran.

Examples of halogen platinum complexes having the following formula:

$$C_3H_6PtB_2X_2$$

are trimethylenedipyridine platinum dichloride, trimethylenebis(alpha-picoline)-platinum dichloride, trimethylenebis-(beta-picoline)-platinum dichloride, trimethylenebis-(gamma-picoline)-platinum dichloride, trimethylenebis-(2-ethylpyridine)-platinum dichloride, trimethylenebis-(3-ethylpyridine)-platinum dichloride, trimethylenebis-(4-ethylpyridine)-platinum dichloride, trimethylenebis-(2-methyl-4-ethylpyridine)-platinum dichloride, trimethylene-2,2'-bipyridyl-platinum dichloride, trimethylenebis-(tetrahydrofurfurylamine)-platinum dichloride, trimethylenebis-(2-methylpiperidine)-platinum dichloride, trimethylenebis-(4-methylpiperidine)-platinum dichloride, trimethylenebis-(2,6-dimethylmorpholine)-platinum dichloride, trimethylenebis-(tetrahydrofuran)-platinum dichloride and trimethylenedipyridine platinum dibromide. Trimethylenedipyridine platinum dichloride is the preferred halogen platinum complex.

The preparation of the halogen platinum complexes having the following formula:

$$C_3H_6PtB_2X_2$$

is well known in the art. Methods for preparing these complexes are described by D. M. Adams and Associates, Journal of the Chemical Society, 1961, page 741; R. D. Gillard and Associates, Journal of Organometallic Chemistry, volume 33, 1971, page 247 to 258, and S. E. Binns and Associates, Journal of the Chemical Society (A), 1969, pages 1227 to 1231. All of these complexes can be prepared in accordance with the general equation:

$$[Pt(C_3H_6)X_2]_4 + 8B \rightarrow 4Pt(C_3H_6)B_2X_2,$$

where B and X are the same as above.

The amount of catalyst used in the hydrosilation process of this invention, i.e., the addition of a silicon compound having an Si-bonded hydrogen atom to a compound having an aliphatic multiple bond, may be the same amount as that used heretofore in processes for the addition of an Si-bonded hydrogen atom to an aliphatic multiple bond. The amount of catalyst is generally at least $10^{-10}$ gram atom, and more preferably from $10^{-8}$ to $10^{-3}$ gram atom of platinum calculated on the weight of metallic platinum per gram atom of Si-bonded hydrogen. However when halogen platinum complexes having the general formula $$C_3H_6PtB_2X_2$$

are used, lower amounts of platinum catalyst, calculation as metallic platinum, are required than were needed in the processes known heretofore for the addition of Si-bonded hydrogen to an aliphatic multiple bond in the presence of a platinum catalyst under the same reaction conditions, i.e., the same reaction time and at temperatures above 34° C.

The temperatures and pressures used in the hydrosilation process of this invention are the same as those which were previously employed for the addition of Si-bonded hydrogen to an aliphatic multiple bond in the presence of a platinum catalyst. The temperature is generally between room temperature and 200° C., preferably between 35° and 150° C., while the pressure used is that of the surrounding atmosphere, i.e., 1 bar or approximately 1 bar. However, if desired, it is possible to employ higher or lower pressures as well.

The process of this invention may be employed whenever monomeric or polymeric silicon compounds having an Si-bonded hydrogen are to be added to monomeric or polymeric compounds having an aliphatic multiple bond. Depending on the type of compounds which are to be added, other monomeric silicon compounds or dimeric or polymeric silicon-containing compounds can be obtained or modified.

The process of this invention may be used in the preparation of monomeric silicon compounds such as, 3-chloropropyltrichlorosilane by reacting trichlorosilane with allyl chloride. Also, the process may be used to prepare 3-chloropropylmethyldichlorosilane by reacting methyldichlorosilane with allyl chloride. Other silicon compounds such as n-propyltrichlorosilane may be prepared by reacting propene with trichlorosilane. Methacryloxypropyltrichlorosilane may be prepared by reacting allylmethyl acrylate with trichlorosilane and vinylmethyldichlorosilane may be prepared by reacting acetylene with methyldichlorosilane.

Examples of dimeric and polymeric silicon containing compounds which can be prepared by the process of this invention are those, for example, obtained from the reaction of vinyltrichlorosilane with trichlorosilane to form bis-(1,2-trichlorosilyl)-ethane. Organosiloxanes having SiC-bonded ester groups can be prepared by the addition of at least one diester of allylsuccinic acid to an organosiloxane containing Si-bonded hydrogen. The process of this invention may also be used to decrease the number of aliphatic multiple bonds in polymers, for example poly-(oxyalkylene)-polyols, by reacting these polymers which contain aliphatic multiple bonds with organopolysiloxanes having at least 2 Si-bonded hydrogen atoms per molecule.

The processes of this invention may be used to modify polymers, in which silicon containing compounds are used to cross-link, i.e., to harden or vulcanize organopolysiloxanes containing alkenyl groups, especially vinyl groups, as well as organopolysiloxanes containing Si-bonded hydrogen. The process of this invention is preferably employed in cross-linking potting or coating compositions, including compositions that are suitable for the preparation of adhesive-repellent coatings, such as those applied to paper or as mold-release compositions, such as those used in the preparation of molded objects from concrete.

If the process of this invention is used for the addition of silicon compounds containing Si-bonded hydrogen to a compound having an aliphatic multiple bond and at least one of the reactants boils at temperatures between 35° and 70° C. or at temperatures below 35° C, and when the application of pressure or the use of a high-boiling reaction medium is not desired, and/or when the aliphatic multiple bond is present as an allyl group, then it is preferred that a halogen platinum complex having the formula $$C_3H_6PtB_2X_2$$

where B and X are the same as above, be employed.

If the process of this invention is to be employed for cross-linking compositions containing organopolysiloxanes having alkenyl groups and organopolysiloxanes containing Si-bonded hydrogen and the compositions are to be cross-linked soon after mixing with the platinum catalyst and at temperatures above 70° C., then it is preferred that a halogen platinum complex having the formula $$A_2PtX_2$$

where A and X are the same as above, be employed. In otherwords, it is preferred that the above platinum catalyst be employed in compositions which are to be cured at temperatures above room temperature and which are free of agents which retard the addition of Si-bonded hydrogen to alkenyl groups at room temperature, such as a dialkylamide.

The halogen platinum complexes used in the following examples as well as those previously described, can be prepared in the following manner. All percents are by weight unless otherwise specified.

(a) About 20 g (40 mmol) of $K_2PtCl_4$ are dissolved in 150 ml of water and mixed with 7.5 g (96 mmol) of alpha-picoline. The mixture which is heated to 70° C. under constant agitation, forms a light yellow precipitate. The mixture is allowed to cool and is then filtered. The filter residue is washed with water and dried at a pressure of 1 microbar. About 15 g, i.e., 69 percent of theory, based on the weight of $K_2PtCl_4$, of bis-(alpha-picoline)-platinum dichloride are obtained.

Pt: calculated: 43.1 percent, found: 43.4 percent (b) The procedure described in (a) above is repeated, except that 7.5 g of beta-picoline is substituted for the alpha-picoline. About 19 g, i.e., 87 percent of theory, based on the weight of K$_2$PtCl$_4$, of bis-(beta-picoline)-platinum dichloride are obtained.

Pt: calculated: 43.5 percent; found: 42.4 percent (c) The procedure described in (a) above is repeated except that 7.5 of gamma-picoline is substituted for the alpha-picoline. About 20 g, i.e., 92 percent of theory, based on the weight of K$_2$PtCl$_4$, of bis-(gamma-picoline)-platinum dichloride are obtained.

Pt: calculated: 43.1 percent; found: 43.9 percent (d) A solution containing 5 g, (12 mmol) of K$_2$PtCl$_4$ in 50 ml of water is mixed with 2.7 g, (24 mmol) of 2-ethylpyridine. The mixture is then stirred for 24 hours at room temperature. A light yellow precipitate is obtained, which is then filtered. The filter residue is washed with water and the water is removed under a pressure of 1 microbar. The filter residue is then washed with n-hexane and dried at 1 microbar. About 4.9 g, i.e., 86 percent of theory, based on the weight of K$_2$PtCl$_4$, of bis-(ethylpyridine)-platinum dichloride are obtained.

Pt: calculated: 40.6 percent; found 41.9 percent (e) The procedure described in (d) above is repeated, except that 2.7 g of 3-ethylpyridine is substituted for the 2-ethylpyridine. About 4.7 g, i.e., 81 percent of theory, based on the weight of K$_2$PtCl$_4$, of bis-(3-ethylpyridine)-platinum dichloride are obtained.

Pt: calculated: 40.6 percent; found: 42.5 percent (f) The procedure described in (d) above is repeated, except that 2.7 g, of 4-ethylpyridine is substituted for the 2-ethylpyridine. About 4.4 g, i.e., 76 percent of theory, based on the weight of K$_2$PtCl$_4$, of bis-(4-ethylpyridine)-platinum dichloride are obtained.

Pt: calculated: 40.6 percent; found: 39.5 percent (g) A solution containing 5 g of K$_2$PtCl$_4$, in 50 ml of water is mixed with 2.9 g (24 mmol) of 2-methyl-4-ethylpyridine. The mixture is then stirred for 48 hours at 40° C. A light yellow precipitate is obtained which is then filtered. The filter residue is washed with water, dried at one microbar, then washed with n-hexane and again dried at one microbar. About 4.2 g, i.e., 70 percent of theory, based on the weight of K$_2$PtCl$_4$, of bis-(2-methyl-4-ethylpyridine)-platinum dichloride are obtained.

Pt: calculated: 38.3 percent; found: 39.5 percent (h) A solution containing 5 g, of K$_2$PtCl$_4$ in 60 ml of water is mixed with 2.9 g (24 mmol) of 4-n-propylpyridine. The mixture is stirred for 48 hours at 30° C. A light yellow precipitate is obtained which is then filtered. The filter residue is washed with water, then washed with n-hexane, filtered and the filter residue is dried at one microbar. About 4.5 g, i.e., 75 percent of theory, based on the weight of K$_2$PtCl$_4$, of bis-(4-n-propylpyridine)-platinum dichloride are obtained.

Pt: calculated: 38.3 percent; found: 37.5 percent (i) About 11 ml of 3-ethylpyridine cooled to a temperature of 9° C., are added under constant stirring to 3 g (2.5 mmol) of [C$_3$H$_6$PtCl$_2$]$_4$. After the mixture has warmed up to room temperature, it is filtered. The filtrate is mixed with water and the colorless precipitate thus obtained is filtered. The filter residue is washed with water and dried at 1 microbar. Approximately 75 percent of theory, based on the weight of the platinum complex, of trimethylenebis-(3-ethylpyridine)-platinum dichloride is obtained.

(k) The procedure described in (i) above is repeated, except that 11 ml of 4-ethylpyridine is substituted for the 3-ethylpyridine. Approximately 75 percent of theory, based on the weight of the platinum complex, of trimethylenebis-(4-ethylpyridine)-platinum dichloride is obtained.

(l) About 1.5 g (1.25 mmol) of [C$_3$H$_6$PtCl$_2$]$_4$ are dissolved in 5 ml of tetrahydrofurfurylamine at 0° C. After stirring for 2 hours, the solution is filtered and the filtrate is mixed dropwise with water. The colorless precipitate thus formed is filtered, the filter residue is washed with water and then dried at one microbar. Approximately 1.6 g, i.e., 65 percent of theory, based on the weight of the platinum complex, of trimethylenebis-(tetrahydrofurfurylamine)-platinum dichloride are obtained.

Pt: calculated: 38.8 percent; found: 41.6 percent (m) About 1.5 g of [C$_3$H$_6$PtCl$_2$]$_4$ are dissolved in 5 ml of 2,6-dimethylmorpholine at 0° C. The mixture is then filtered and the filtrate mixed with water. The colorless precipitate thus formed is filtered. The filter residue is washed with water, then 5 ml of n-hexane and dried at 1 microbar. About 2.4 g, i.e., 75 percent of theory, based on the weight of the platinum complex, of trimethylene-bis-(2,6-dimethylmorpholine)platinum dichloride are obtained.

Pt: calculated: 36.2 percent; found: 36.8 percent (n) The process described in (m) above is repeated, except that 5 ml of 2-methylpiperidine is substituted for the 2,6-dimethylmorpholine. About 1.25 g, i.e., 62 percent of theory, based on the platinum complex, of trimethylenebis-(2-methylpiperidine)-platinum dichloride are obtained in the form of a light yellow product.

Pt: calculated: 38.5 percent; found: 39.0 percent (o) The procedure described in (m) above is repeated, except that 5 ml of 4-methylpiperidine is substituted for 2,6-dimethylmorpholine. About 1.0 g, i.e., 50 percent of theory based on the weight of the platinum complex, of trimethylenebis(4-methylpiperidine)-platinum dichloride is obtained.

Pt: calculated: 38.5 percent; found: 37.3 percent (p) About 1.2 g (1 mmol) of [C$_3$H$_6$PtCl$_2$]$_4$ are dissolved in 10 ml of tetrahydrofuran at 0° C. After the excess tetrahydrofuran has been distilled off, 1.8 g, i.e., 100 percent of theory, based on the weight of the platinum complex, of trimethylenebis-(tetrahydrofuran)-platinum dichloride are obtained in the form of an oil.

EXAMPLES 1 through 5

A mixture containing 100 parts by weight of a trimethylsiloxy end-blocked diorganopolysiloxane which consists of 99.5 mol percent of dimethylsiloxane and 0.5 ml percent of vinylmethylsiloxane units and having an mkp value of 580 as determined in a Brabender-plastograph at 25° C. and at 60 rpm, 45 parts by weight of pyrogenically produced silicon dioxide having a surface area of 270 m$^2$/g and 7 parts by weight of a dimethylpolysiloxane diol containing 4.0 weight percent of Si-bonded hydroxyl groups, is mixed with 5 ml of a methylenechloride solution containing 20 ppm, based on the weight of the above mixture, of platinum, calculated as the element, in the form of the halogen platinum complex shown in the following Table I. The mixture thus obtained is mixed with an equal amount of a mixture containing 100 parts by weight of a trimethylsiloxy and end-blocked diorganopolysiloxane containing 99.5 mol percent of dimethylsiloxane and 0.5 mol percent of vinylmethylsiloxane units having an mkp value of 580 as determined in a Brabender-plastograph, 45 parts by weight of pyrogenically produced silicon dioxide having a surface area of 270 m$^2$/g, 7 parts by weight of a dimethylpolysiloxane diol containing 4.0 percent by weight of Si-bonded hydroxyl groups, and 0.55 parts by weight of a trimethylsiloxy end-blocked methylhydrogenpolysiloxane which has a viscosity of 80 cP at 23° C. The time required before noticeable cross-linking occurs at 25° C. is shown in the following table:

TABLE I

| Example | Halogen-platinum complex | Number of days elapsed before cross-linking is observed |
|---|---|---|
| 1 | Bis-(alpha-picoline)-platinum-dichloride | 20 |
| 2 | Bis-(beta-picoline)-platinum-dichloride | 20 |
| 3 | Bis-(gamma-picoline)-platinum-dichloride | 20 |
| 4 | Bis-(4-ethylpyridine)-platinum dichloride | 15 |
| 5 | Bis-(2-methyl-4-ethylpyridine)-platinum dichloride | 25 |

In a comparison example, a similar composition which contains $H_2PtCl_6 \cdot 6H_2O$ instead of the halogen platinum complex used in Examples 1 to 5, cross-links at room temperature within 3 days when the composition is free of inhibitors. This is shown in the table of U.S. Pat. No. 3,461,185, to Brown.

Even at 45° C., the "pot life", i.e., the time required before noticeable crosslinking occurs, is one day when halogenplatinum complexes are employed having the following formula:

$A_2PtX_2$, in which A and X are the same as above. Moreover, it is possible to pour curable compositions containing the halogen platinum complexes into previously used molds while the molds are still warm.

Table II shows the average mechanical properties of elastomers obtained from compositions prepared in accordance with Examples 1 through 5, which have been heated for 15 minutes at 165° C. under a pressure of 100 bar.

TABLE II

|  | After Crosslinking | After elastomers have been heated for 4 hrs to 200° C. |
|---|---|---|
| Tensile strength, (kp/cm$^2$) | 70 | 73 |
| Elongation at rupture, percent | 800 | 700 |
| Resistance to additional tearing, (kp/cm) | 45 | 40 |
| Shore-A, hardness | 58 | 60 |

EXAMPLES 7 THROUGH 9, AS WELL AS COMPARISON EXAMPLES V$_1$-V$_3$

A mixture containing methyldichlorosilane, allyl chloride and platinum in the form of the composition shown in Table III and at a molar ratio of $1:1:2.5 \cdot 10^{-5}$ is refluxed until the reflux temperature has increased to 90° C. and propene is no longer evolved. The propene is generated by the following undesirable side reaction:

$$CH_3SiCl_2H + CH_2=CHCH_2Cl \rightarrow CH_3SiCl_3 + CH_2=CHCH_3$$

TABLE III

| Examples | Pt composition | Elaspsed time ta in minutes until reaction begins | Elapsed time to end of reaction incl. ta in min. | Cl(CH$_2$)$_3$-SiCl$_2$(CH$_3$) mol percent | CH$_3$-SiCl$_3$ mol percent |
|---|---|---|---|---|---|
| 6 | C$_3$H$_6$PtB$_2^1$Cl$_2$ | 1 | 10 | 72 | 28 |
| 7 | C$_3$H$_6$PtB$_2^2$Cl$_2$ | 3 | 60 | 72 | 28 |
| 8 | C$_3$H$_6$PtB$_2^3$Cl$_2$ | 3 | 50 | 71 | 29 |
| 9 | C$_3$H$_6$PtB$_2^4$Cl$_2$ | 4 | 60 | 70 | 30 |
| Comparison Examples | | | | | |
| V$_1$ | (+) | 3 | 120 | 63 | 37 |
| V$_2$ | H$_2$PtCl$_6$ . 6H$_2$O | 10 | 45 | 54 | 46 |
| V$_3$ | [Pt(C$_2$H$_4$)Cl$_2$]$_2$ | 5 | 25 | 61 | 39 |

B$^1$ = pyridine
B$^2$ = alpha-picoline
B$^3$ = beta-picoline
B$^4$ = gamma-picoline
(+)The Pt composition was prepared by heating 1g of H$_2$PtCl$_6$ . 6H$_2$O in 200 ml of cyclohexanone to 100° C. for 1 hour and thereafter drying the resultant solution over anhydrous sodium sulfate.

EXAMPLE 10

A mixture containing 200 g of a dimethylpolysiloxane containing dimethylhydrogen siloxane terminal units and having an average of 32 dimethylsiloxane units per molecule, 100 ml of toluene and 10 mg of trimethylenedipyridine platinum dichloride is heated at 115° to 120° C. While the heated mixture is being stirred, 55 g of allylsuccinic acid di-n-butylester are added dropwise. After the addition of the ester has been completed, stirring at 115° to 120° C. is continued for an additional 5 hours.

After the toluene and the excess ester have been distilled off, essentially a 100 percent yield of dimethylpolysiloxane having an average of 32 dimethylsiloxane units per molecule and whose terminal units are those corresponding to the following formula:

$$CH_3(CH_2)_3OOCCH_2CH[COO(CH_2)_3CH_3](CH_2)_3Si(CH_3)_2O-$$

is obtained in the form of an oil. After filtering the oil through Fuller's earth ["bleaching earth"], a product is obtained which has a viscosity of 222 cP at 20° C., 47 cP at 23° C. and 15 cP at 80° C.

COMPARISON EXAMPLE V$_4$

The procedure described in Example 10 was repeated, except that palladium or rhodium on activated carbon containing 5 weight percent of metallic palladium or rhodium based on the weight of the activated carbon were substituted for the trimethylenedipyridine platinum dichloride.

COMPARISON EXAMPLE V₅

The procedure described in Example 10 was repeated, except that the same amount of platinum in the form of $H_2PtCl_6.6H_2O$ was substituted for the trimethylenedipyridine platinum dichloride.

The yield in comparison examples $V_4$ and $V_5$ was only 90 to 95 weight percent of theory and approximately 15 hours were required to achieve that yield.

EXAMPLE 11

The procedure described in Example 10 is repeated, except that 10 mg of bis-(gamma-picoline)-platinum dichloride are substituted for the trimethylenedipyridine platinum dichloride. The time required to obtain a 100 percent yield of the desired oil is about 5 hours.

What is claimed is:

1. A process for preparing organosilicon compounds containing carbon-silicon bonds which comprises reacting a silicon compound containing at least one Si-bonded hydrogen with a compound containing an aliphatic multiple bond in the presence of a catalytic amount of at least one halogen platinum complex selected from the group consisting of $$A_2PtX_2, C_3H_6PtB_2X_2$$

and mixtures thereof, in which A represents a pyridine ring containing 1 or 2 alkyl radicals having from 1 to 3 carbon atoms, B is selected from the group consisting of 5- or 6-membered heterocyclic radicals and linked 5- or 6-membered heterocyclic radicals containing 1 or 2 heteroatoms and X represents chlorine.

2. The process of claim 1, wherein the halogen platinum complex has the formula $$A_2PtX_2$$

in which A represents a pyridine ring containing 1 or 2 alkyl radicals having from 1 to 3 carbon atoms and X represents chlorine.

3. The process of claim 1 wherein the halogen platinum complex has the formula $$C_3H_6PtB_2X_2$$

in which B is selected from the group consisting of 5- or 6-membered heterocyclic radicals and linked 5- or 6-membered heterocyclic radicals containing 1 or 2 heteroatoms and X represents chlorine.

4. The process of claim 3 wherein the halogen platinum complex is trimethylenedipyridine platinum dichloride.

5. The process of claim 1 wherein the halogen platinum complex is present in an amount of from $10^{-10}$ to $10^{-3}$ gram atom of platinum based on metallic platinum per gram atom of Si-bonded hydrogen.

6. The process of claim 1 wherein the reaction is conducted at a temperature above about 35° C. up to 200° C.

7. The process of claim 1, wherein the reaction is conducted at a temperature up to 70° C. in the presence of a platinum complex having the formula $$C_3H_6PtB_2X_2,$$

where B is selected from the group consisting of 5- or 6-membered heterocyclic radicals and linked 5- or 6-membered heterocyclic radicals containing 1 or 2 heteroatoms and X is chlorine.

8. The process of claim 1, wherein the reaction is conducted at a temperature above 70° C. in the presence of a platinum complex having the formula $$A_2Pt\,X_2$$

where A is a pyridine ring containing 1 or 2 alkyl radicals having from 1 to 3 carbon atoms and X is chlorine.

* * * * *